(12) United States Patent
Klaue (10) Patent No.: US 9,522,009 B2
(45) Date of Patent: Dec. 20, 2016

(54) DEVICE FOR FORMING A BORE TO FACILITATE INSERTION OF AN ARCUATE NAIL INTO A BONE

(75) Inventor: Kaj Klaue, Savosa (CH)

(73) Assignee: Biedermann Technologies GmbH & Co. KG, Donaueschingen (DE)

(*) Notice: Subject to any disclaimer, the term of this patent is extended or adjusted under 35 U.S.C. 154(b) by 446 days.

(21) Appl. No.: 12/781,168

(22) Filed: May 17, 2010

(65) Prior Publication Data

US 2010/0292722 A1 Nov. 18, 2010

(30) Foreign Application Priority Data

May 18, 2009 (CH) .......................... 777/09

(51) Int. Cl.
*A61B 17/17* (2006.01)
*A61B 17/16* (2006.01)
*A61B 17/84* (2006.01)

(52) U.S. Cl.
CPC ....... *A61B 17/1642* (2013.01); *A61B 17/1682* (2013.01); *A61B 17/846* (2013.01)

(58) Field of Classification Search
CPC ............ A61B 17/1615; A61B 17/1631; A61B 17/1633; A61B 17/1642; A61B 17/1662; A61B 17/1682; A61B 17/17; A61B 17/1717; A61B 17/1739
USPC ......... 606/62–68, 79, 80, 86 R, 96, 97, 103, 606/104, 167, 168, 170, 171, 172, 180; 623/21.18
See application file for complete search history.

(56) References Cited

U.S. PATENT DOCUMENTS

| | | | |
|---|---|---|---|
| 1,630,239 A * | 5/1927 | Binkley et al. | 606/180 |
| 1,677,337 A * | 7/1928 | Grove | 606/180 |
| 2,668,536 A * | 2/1954 | Farries et al. | 606/167 |
| 3,835,858 A * | 9/1974 | Hagen | 606/180 |
| 3,847,154 A * | 11/1974 | Nordin | 606/180 |
| 4,541,423 A * | 9/1985 | Barber | 606/80 |
| 4,877,019 A | 10/1989 | Vives | |
| 5,041,115 A | 8/1991 | Frigg et al. | |
| 5,053,035 A | 10/1991 | McLaren | |
| 5,190,548 A * | 3/1993 | Davis | 606/80 |
| 5,312,406 A | 5/1994 | Brumfield | |
| 5,395,188 A * | 3/1995 | Bailey et al. | 408/127 |
| 5,624,447 A | 4/1997 | Myers | 606/96 |
| 5,700,265 A * | 12/1997 | Romano | 606/80 |
| 5,720,749 A * | 2/1998 | Rupp | 606/79 |
| 5,735,899 A * | 4/1998 | Schwartz et al. | 606/261 |
| 5,855,579 A | 1/1999 | James et al. | |
| 5,871,486 A | 2/1999 | Huebner et al. | |

(Continued)

FOREIGN PATENT DOCUMENTS

CA 2 608 286 A1 11/2006
DE 133162 10/1901

(Continued)

OTHER PUBLICATIONS

International Search Report, mailed Jan. 8, 2009, corresponding to PCT/CH2008/000474, 8 pages.

(Continued)

*Primary Examiner* — Lynnsy Summitt
(74) *Attorney, Agent, or Firm* — Lewis Roca Rothgerber Christie LLP (57) ABSTRACT

A device for forming a circular arc-shaped bore includes: a stiff circular arc-shaped tube having a central axis; a flexible shaft insertable into the tube; and a head mountable to a first end of the shaft.

35 Claims, 10 Drawing Sheets

(56) References Cited

U.S. PATENT DOCUMENTS

| | | | |
|---|---|---|---|
| 5,996,582 A * | 12/1999 | Turnbull | 128/207.29 |
| 6,015,411 A * | 1/2000 | Ohkoshi et al. | 606/80 |
| 6,018,094 A * | 1/2000 | Fox | 606/191 |
| 6,074,392 A | 6/2000 | Durham | |
| 6,309,396 B1 * | 10/2001 | Ritland | 606/96 |
| 6,419,678 B1 * | 7/2002 | Asfora | 606/96 |
| 6,447,514 B1 * | 9/2002 | Stalcup et al. | 606/63 |
| 6,579,293 B1 * | 6/2003 | Chandran | 606/64 |
| 6,607,530 B1 * | 8/2003 | Carl et al. | 606/914 |
| 6,702,816 B2 | 3/2004 | Bühler | |
| 6,709,436 B1 | 3/2004 | Hover et al. | |
| 6,740,090 B1 * | 5/2004 | Cragg et al. | 606/79 |
| 6,755,862 B2 * | 6/2004 | Keynan | 623/16.11 |
| 6,790,210 B1 * | 9/2004 | Cragg et al. | 606/80 |
| 6,830,572 B2 * | 12/2004 | McDevitt et al. | 606/232 |
| 7,569,056 B2 * | 8/2009 | Cragg et al. | 606/79 |
| 7,875,059 B2 * | 1/2011 | Patterson et al. | 606/261 |
| 7,879,037 B2 * | 2/2011 | Brunnett et al. | 606/79 |
| 7,922,720 B2 * | 4/2011 | May et al. | 606/80 |
| 7,963,967 B1 * | 6/2011 | Woods | 606/79 |
| 8,016,846 B2 * | 9/2011 | McFarlin et al. | 606/170 |
| 8,034,115 B2 * | 10/2011 | Reiley | 623/21.18 |
| 8,062,295 B2 * | 11/2011 | McDevitt et al. | 606/60 |
| 8,066,706 B2 | 11/2011 | Schlienger et al. | |
| 2002/0038129 A1 * | 3/2002 | Peters et al. | 606/167 |
| 2002/0099401 A1 * | 7/2002 | Bonutti | 606/170 |
| 2003/0009172 A1 * | 1/2003 | Bonutti | 606/96 |
| 2005/0177168 A1 * | 8/2005 | Brunnett et al. | 606/80 |
| 2005/0267481 A1 * | 12/2005 | Carl et al. | 606/79 |
| 2006/0129153 A1 | 6/2006 | Klaue et al. | |
| 2006/0200141 A1 | 9/2006 | Janna et al. | |
| 2006/0229624 A1 * | 10/2006 | May et al. | 606/79 |
| 2006/0241605 A1 | 10/2006 | Schlienger et al. | |
| 2007/0112432 A1 * | 5/2007 | Reiley | 623/21.18 |
| 2007/0225721 A1 * | 9/2007 | Thelen et al. | 606/80 |
| 2007/0270846 A1 * | 11/2007 | Metzinger | 606/64 |
| 2007/0276385 A1 | 11/2007 | Schlienger et al. | |
| 2007/0288017 A1 | 12/2007 | Kaup | |
| 2008/0140078 A1 * | 6/2008 | Nelson et al. | 606/80 |
| 2009/0131940 A1 * | 5/2009 | Brunnett et al. | 606/80 |
| 2009/0177240 A1 * | 7/2009 | Perez | 606/86 R |
| 2009/0182433 A1 * | 7/2009 | Reiley et al. | 623/18.11 |
| 2009/0187191 A1 * | 7/2009 | Carl et al. | 606/80 |
| 2009/0292287 A1 * | 11/2009 | Cragg et al. | 606/79 |
| 2010/0016906 A1 * | 1/2010 | Abdou | 606/86 R |
| 2010/0042157 A1 * | 2/2010 | Trieu | 606/255 |
| 2010/0076502 A1 * | 3/2010 | Guyer et al. | 606/86 R |
| 2010/0114098 A1 * | 5/2010 | Carl | 606/80 |
| 2010/0137923 A1 * | 6/2010 | Greenhalgh et al. | 606/86 R |
| 2010/0191248 A1 * | 7/2010 | Mehta et al. | 606/96 |
| 2010/0204700 A1 * | 8/2010 | Falahee | 606/80 |
| 2010/0222820 A1 * | 9/2010 | Trieu | 606/255 |
| 2010/0256644 A1 * | 10/2010 | Stearns et al. | 606/80 |
| 2010/0292722 A1 * | 11/2010 | Klaue | 606/167 |
| 2010/0305623 A1 * | 12/2010 | Klaue | 606/329 |
| 2011/0160731 A1 * | 6/2011 | Bleich et al. | 606/79 |
| 2011/0224735 A1 * | 9/2011 | Pagano | 606/289 |
| 2011/0270293 A1 * | 11/2011 | Malla et al. | 606/170 |
| 2011/0276052 A1 * | 11/2011 | Hasselman | 606/87 |
| 2011/0282397 A1 * | 11/2011 | Richter et al. | 606/304 |
| 2011/0288555 A1 * | 11/2011 | Szanto | 606/84 |
| 2012/0004728 A1 * | 1/2012 | Kohm et al. | 623/17.11 |

FOREIGN PATENT DOCUMENTS

| | | |
|---|---|---|
| DE | 76 07 981 | 11/1977 |
| DE | 7607981 | 11/1977 |
| JP | 2007508852 | 4/2007 |
| WO | WO 90/12550 | 11/1990 |
| WO | WO 03/017822 A2 | 3/2003 |
| WO | WO 2004/089255 A1 | 10/2004 |
| WO | WO 2006/119659 A1 | 11/2006 |
| WO | WO 2007/053960 A1 | 5/2007 |
| WO | WO 2007/120539 A2 | 10/2007 |
| WO | WO 2008/099176 A1 | 8/2008 |
| WO | WO 2009067831 A1 * | 6/2009 |

OTHER PUBLICATIONS

Written Opinion (English translation), mailed Jan. 8, 2009, corresponding to PCT/CH2008/000474, 7 pages.

International Search Report, mailed Sep. 2, 2010, for Application No. PCT/IB2010/001089, 3 pages.

Written Opinion (English translation), mailed Sep. 2, 2010, for Application No. PCT/IB2010/001089, 6 pages.

* cited by examiner

Fig. 11k 150-220·10³ N/mm²...

DEVICE FOR FORMING A BORE TO FACILITATE INSERTION OF AN ARCUATE NAIL INTO A BONE

CROSS-REFERENCE TO RELATED APPLICATION(S)

The present application claims priority to and the benefit of Swiss Patent Application CH 00777/09, filed May 18, 2009, with the Swiss Patent Office, the disclosure of which is incorporated herein by reference.

BACKGROUND

Field

The invention relates to a device for forming or drilling a circular arc-shaped bore, a kit including such a device, and a method of forming or drilling a circular arc-shaped bore using such a device.

Description of Related Art

In some applications, it may be desirable to place a bore in a controlled manner along a circular arc-shaped channel. Specifically in the field of bone surgery, practitioners may want to insert arcuate-shaped implants into the bone in a controlled manner and without unnecessary loss of bone material. There has not been a tool developed for forming circular arc-shaped bores, to facilitate insertion of a circular arc-shaped implant, for example, an arcuate nail. A circular arc-shaped bore allows for an unproblematic insertion of a monomorphic implant, since any shape of the bore departing from the circular arc may lead to jamming of the implant to be inserted.

SUMMARY OF THE INVENTION

Embodiments of the invention provide a device for forming or drilling a circular arc-shaped bore, a kit including the device and at least one implant for a heel which is formed as, for example, a bone nail, and a method of forming or drilling a circular arc-shaped bore using such a device.

Embodiments of the invention may provide for an exactly circular arc-shaped bore to be manufactured.

In one embodiment the device comprises a motor drive for a flexible shaft. Thereby, the flexible shaft may be connected via its rear end with a drive machine, wherein a clamping means of the drive machine is disposed and axially fixed at a rear end of a stiff tube located around the flexible shaft. Further, an outer diameter of the flexible shaft is dimensioned corresponding to an inner diameter of the tube, such that the flexible shaft has only a small tolerance within the tube. Due to the small tolerance and the guidance of the flexible shaft along its entire length within the tube, the helically curved wire windings of the flexible shaft will not widen due to the torque to be transferred towards the tool head, such that despite the bending elasticity, a high torsional stiffness of the flexible shaft is realized. The device can be provided with a handle.

In another embodiment a device comprises a push cup, which is fixed at the rear end of the flexible shaft and can be attached to the rear end of the tube. A driving pin which can be clamped in a driving machine extends from the push cup. By applying a feeding force onto the driving machine, the tube may be moved along with the flexible shaft in a frontward (i.e., advancing) direction.

In a further embodiment, coupling means are arranged at the front end of the flexible shaft, by which a tool head can be removably coupled to the flexible shaft. The flexible shaft is supported by the push cup in an axially rigid manner at the rear end of the tube, while the tool is disposed axially at the front end of the tube.

The assembly of the flexible shaft and the tool head may be carried out according to the following steps:

a) The flexible shaft may be inserted into the tube from the rear end, and the push cup, which in a further embodiment may be formed in a ring-like manner as a push ring, is either rotated as a nut on the flexible shaft in frontward or rearward direction, or is shifted in a rastered manner by a spring system on the flexible shaft from notch to notch;
b) the flexible shaft is moved slightly frontward and off the front opening of the tube, and the tool head is hooked with a rigid raster system; and
c) the push cup or the push ring is moved, for example, in the embodiment including the raster system, on the flexible shaft from a rear side against the rear end of the tube, wherein the flexible shaft is biased, since the tool head is disposed at the front end of the tube.

In a further embodiment, the tool head is movable solely by the flexible shaft.

In a further embodiment the radius of curvature of the central axis of the tube may be 240 mm at maximum, preferably 210 mm at maximum.

In a further embodiment the radius of curvature of the center axis of the tube may be at least 130 mm, preferably at least 200 mm.

In another embodiment the curvature of each infinitesimal section of the stiff tube may correspond to a radius of curvature of the central axis, which may be at least 130 mm.

In a further embodiment, the tube includes an outer diameter $d_a$, which may be 16 mm at maximum, preferably 13 mm at maximum.

In a further embodiment the tube may have an inner diameter $d_i$ in the range of 3-7 mm.

In another embodiment the tube may have a mantle thickness of at least 0.5 mm, preferably at least 1.5 mm.

In a further embodiment the tube may have a tube length of at least 5 cm, and 35 cm at maximum.

In a further embodiment the tube may be manufactured from stainless steel.

In a further embodiment the tube may be manufactured from a material having an E-module of at least $150 \cdot 10^3$ N/mm$^2$, and may have a bending stiffness E·I of at least $1.3 \cdot 10^6$ N mm$^2$.

The following are examples of material properties, taken from Dubbel, “Taschenbuch für den Maschinenbau”, 21. Ed., 2005, Springer-Verlag:

Stainless steels: E-module $150\text{-}220 \cdot 10^3$ N/mm$^2$

For the tube the following values are obtained for the axial 2$^{nd}$ order moment of area and the bending stiffness:

Typical value for the bending stiffness (tube having outer diameter $d_a$=12 mm and inner diameter $d_i$=7 mm): Axial 2$^{nd}$ order moment of area [tube: $I=I_x=I_y=\pi(d_a^4-d_i^4)/64$] for $d_a$=12 mm and $d_i$=7 mm yields, $I_x$=900 mm$^4$, Bending stiffness E·I=$135\text{-}198 \cdot 10^6$ N mm$^2$.

Minimum value for the bending stiffness (tube having inner diameter $d_i$=3 mm and wall thickness 0.5 mm): Axial 2$^{nd}$ order moment of area [tube: $I=I_y=\pi(d_a^4-d_1^4)/64$] for $d_a$=4 mm and $d_i$=3 mm yields, $I_x$=8.6 mm$^4$, Bending stiffness E·I=$1.3\text{-}1.9 \cdot 10^6$ N mm$^2$.

In another embodiment the tool head may have an outer diameter D, where the ratio $d_a$/D between an outer diameter $d_a$ of the tube and the outer diameter D may be 0.95 at maximum, preferably 0.92 at maximum. Typically, the ratio is $d_a$/D=10/11.

In a further embodiment the device may further include a target device which can be fixed at a part of the body to be treated, where the target device includes a circular arc-shaped guide for adjustable receipt of the stiff tube. The target device is preferably formed as a C-arc.

In a further embodiment the guide may include two or more target rings. The centers of the target rings lie on a circular arc, the radius of which corresponds to the curvature of the central axis of the tube, and where an angle of the arc may be between at least 10° and 45° at maximum.

In another embodiment the target device has a first end that can be disposed at the surface of a bone, a second end, and a fixation carriage that can be disposed at the surface of a bone. The fixation carriage is slidably supported in a radial direction relative to the arcuate-shaped target device at the second end of the target device, for example, by means of a dove tail guide extending substantially in a radial direction.

In another embodiment the fixation carriage can be mounted to the bone using Kirschner wires.

In a further embodiment the tool head may be provided with axial perforations for the removal of chips of bone material from the bore. The perforations penetrate the tool head in an axial direction and open into the cavity of the flexible shaft, which is formed as a hollow shaft.

In a specific embodiment of the kit, the bone nail may be manufactured from unresorbable material, preferably from stainless steel or titanium or CrCo.

The following are material properties, taken from Dubbel, "Taschenbuch für den Maschinenbau", 21. Ed., 2005, Springer-Verlag:
 a) Stainless steels: E-module 150-220·10³ N/mm²
 b) Titanium: E-module 100-105·10³ N/mm²
 c) Titanium alloy: E-module 110-130·10³ N/mm²"

In an embodiment an implant formed as a bone nail may have an outer diameter $D_I$ ranging from 9 to 13 mm.

In a further embodiment the front part of the bone nail may be formed in an elastically bendable manner.

In another embodiment a front part of the bone nail may be less stiff than a rear part. In the front part of the bone nail, longitudinal channels may be provided, such that the front part has a smaller and/or weaker cross-section than the rear part. The front part may therefore be made more flexible than the stiff rear part. The front part, as well as the rear part, of the bone nail may make up 30% to 70% of the entire length of the bone nail.

In another embodiment the bone nail may have, at least in the front part, a longitudinal slit.

In another embodiment the bone nail may include, at least in the front part, a shamrock-shaped cross-section.

In another embodiment the rear part of the bone nail may be formed to be stiff.

In a further embodiment the bone nail may have, at least in the front part, a cavity that is parallel to the longitudinal axis. The bone nail may also be provided in tubular shape, where the half part related to the tip may have a wall thickness of 0.5 mm. Further, the front part of the bone nail, which is formed in tubular shape, may comprise a slit.

For the flexible front part of the implant the following values are obtained for the axial $2^{nd}$ order moment of area and the bending stiffness:
 Minimum axial $2^{nd}$ order moment of area for an outer diameter $D_I$=9 mm and wall thickness of 0.5 mm (inner diameter $d_I$=8 mm) [tube: $I=I_x=I_y=\pi(D_I^4-d_I^4)/64$] for $D_I$=9 mm and $d_I$=8 mm, it follows that $I_x$=12 mm⁴.
 Maximum axial $2^{nd}$ order moment of area for outer diameter $D_I$=13 mm and wall thickness of 0.5 mm (inner diameter $d_I$=12 mm) [tube: $I=I_x=I_y=\pi(D_I^4-d_I^4)/64$] for $D_I$=13 mm and $d_I$=12 mm, it follows that $I_x$=384 mm⁴.

The following are examples of material properties, taken from Dubbel, Dubbel, "Taschenbuch für den Maschinenbau", 21. Ed., 2005, Springer-Verlag
 a) Stainless steels: E-module 150-220·10³ N/mm².
  Minimum bending stiffness E·I=18.2-26.6·10⁶ N mm²
  Maximum bending stiffness E·I=57.6-84.5·10⁶ N mm²
 b) Titanium: E-module 100-105·10³ N/mm²
  Minimum bending stiffness E·I=12.1-12.7·10⁶ N mm²
  Maximum bending stiffness E·I=38.4-40.3·10⁶ N mm²
 c) Titanium alloys: E-module 110-130·10³ N/mm²
  Minimum bending stiffness E·I=13.3-15.7·10⁶ N mm²
  Maximum bending stiffness E·I=42.2-49.9·10⁶ N mm²

The bending stiffness B is evaluated according to Dubbel, "Taschenbuch für den Maschinenbau", 21. Ed., 2005, Springer-Verlag in agreement with the formula: B=E×I, wherein I corresponds to the axial $2^{nd}$ order moment of area in mm⁴ and E is the E-module in N/mm². The axial $2^{nd}$ order moment of area I depends on the selected bending axis.

In another embodiment the front part of the bone nail can be plastically deformed.

In another embodiment the front part of the bone nail may include a bending stiffness of at least 12·10⁶ N mm², preferably at least 15·10⁶ N mm².

In another embodiment, the front part of the bone nail may include a bending stiffness of 85·10⁶ N mm² at maximum, preferably 60·10⁶ N mm² at maximum. The front part may have a maximum of 50% of the stiffness of the rear part.

In another embodiment the bone nail may have a nail length $L_I$ of 12-50 cm.

In another embodiment the curvature radius of the bone nail may be 240 mm at maximum, preferably 210 mm at maximum.

In another embodiment the ratio $L_I/D_I$ between a nail length $L_I$ and a diameter $D_I$ may be less than 16, preferably less than 14.

In a further embodiment the implant may have at least a transverse bore for receiving a locking screw, wherein the longitudinal axis of the transverse bore preferably lies within the curvature plane of the bone nail.

In another embodiment the curvature radius of the bone nail may be at least 130 mm, preferably at least 200 mm.

In another embodiment the bone nail may include an intermediate part between the front part and the rear part, the stiffness of intermediate part increasing towards the rear part.

An application of the device may be for forming a circular arc-shaped bore in the bone.

A further application of the device relates to its application in facilitating Tibio-Calcaneal Arthrodesis.

BRIEF DESCRIPTION OF THE DRAWINGS

The invention and further aspects of the invention are explained in more detail in the following description, in conjunction with drawings of several embodiments, in which.

DETAILED DESCRIPTION

The embodiment of the device 9 shown in FIGS. 1 through 4 substantially includes a stiff circular arc-shaped tube 10 having a central axis 14, a flexible shaft 11 inside the tube 10 and a tool head 12 mountable to a front part of the flexible shaft 11. Further, the device 9 may be provided with a motor drive (not illustrated) for rotationally driving the flexible shaft 11 and the tool head 12.

To provide for an axial feed, a push cup 15 may be fixed at a rear end of the flexible shaft 11. A drive pin 22 is terminally disposed and extends from the push cup 15, and can be clamped into a drive machine. By exerting a feed force to the drive machine, the tube 10 can be fed forward in conjunction with the flexible shaft 11. At the front part of the flexible shaft 11, coupling means (not illustrated) are located, by means of which the tool head 12 can be removably coupled to the flexible shaft 11. The coupling means provide a pre-tension of the flexible shaft 11 after fixation of the tool head 12 at the front part of the flexible shaft 11. The flexible shaft 11 is rigidly supported axially at the rear end of the tube 10 by means of the push cup 15, while the tool head 12 is axially attached at the front end of the tube 10, such that after the fixation of the tool head 12 a pre-tension can be exerted onto the flexible shaft 11. Between the front end of the flexible shaft 11 and the tool head 12, and between the rear end of the flexible shaft 11 and the push cup 15; the pre-tension results in a frictional force. The tool head 12 is driven rotationally by the flexible shaft 11 and axially by the tube 10. In some embodiments, the central axis 14 of the stiff tube 10 has a constant radius of curvature along the entire length of the tube 10 and/or a constant radius or curvature for each infinitesimal section.

The tool head 12 has an outer diameter D, which is larger than an outer diameter of the tube 10. The flexible shaft is formed as an elastically bendable hollow shaft and has an outer diameter that corresponds to an inner diameter $d_i$ of the tube 10. Further, the tool head 12 may be provided with perforations 36 for removing chips of bone material, for example, from a bore being formed or drilled. The perforations 36 penetrate or traverse the tool head 12 in an axial direction and open into a cavity of the flexible shaft 11. The chips of bone material produced during the drilling process are transferred through the perforations 36 into the cavity of the flexible shaft 11, and are then evacuated through the cavity.

The device 9 may be movably mounted to a target device 13, which can be fixed to a foot, and which is to be positioned such that the stiff tube 10 can be axially inserted into a bone in conjunction with the flexible shaft 11 and the tool head 12. The target device 13 may be formed as a C-arc and may include a circular arc-shaped guide 16 for adjustably or movably coaxially receiving the stiff tube 10. In the embodiment shown herein, the circular arc-shaped guide 16 includes two target rings 17, the centers of which lie on a circular arc having a radius of curvature which corresponds to the radius of curvature of the central axis 14 of the tube 10, and which in one embodiment includes an angle of arc of 25°.

The target device 13 further includes a first end 20, which can be disposed at a surface of a bone and which has a tip 35, a fork-shaped second end 21 and a fixation carriage 18, which can also be disposed at the surface of the bone. The fixation carriage 18 has in the embodiment illustrated two jaws 23, which are laterally disposed adjacent to the stiff tube 10. The fixation carriage 18 may be slidably supported at the second end 21 of the target device 13 in a radial direction with respect to the arc-shaped target device 13, wherein the two jaws 23 are guided by means of dove tail guides 24, which extend in a radial direction. The two jaws 23 may be provided with bores for receiving Kirschner wires 19, wherein the bores are arranged parallel to the plane of the central axis 14 of the stiff tube 10, such that the target device 13 is mountable to the bone by means of the Kirschner wires 19. The assembly of the tool head 12 is carried out after the fixation of the target device 13 at the foot, wherein the stiff tube 10 can be retracted to an extent, such that the tool head 12 can be inserted between the front end of the stiff tube 10 and the surface of the bone and between the two jaws 23 of the fixation carriage 18, and such that it can be mounted at the front end of the flexible shaft 11.

Figure 1:
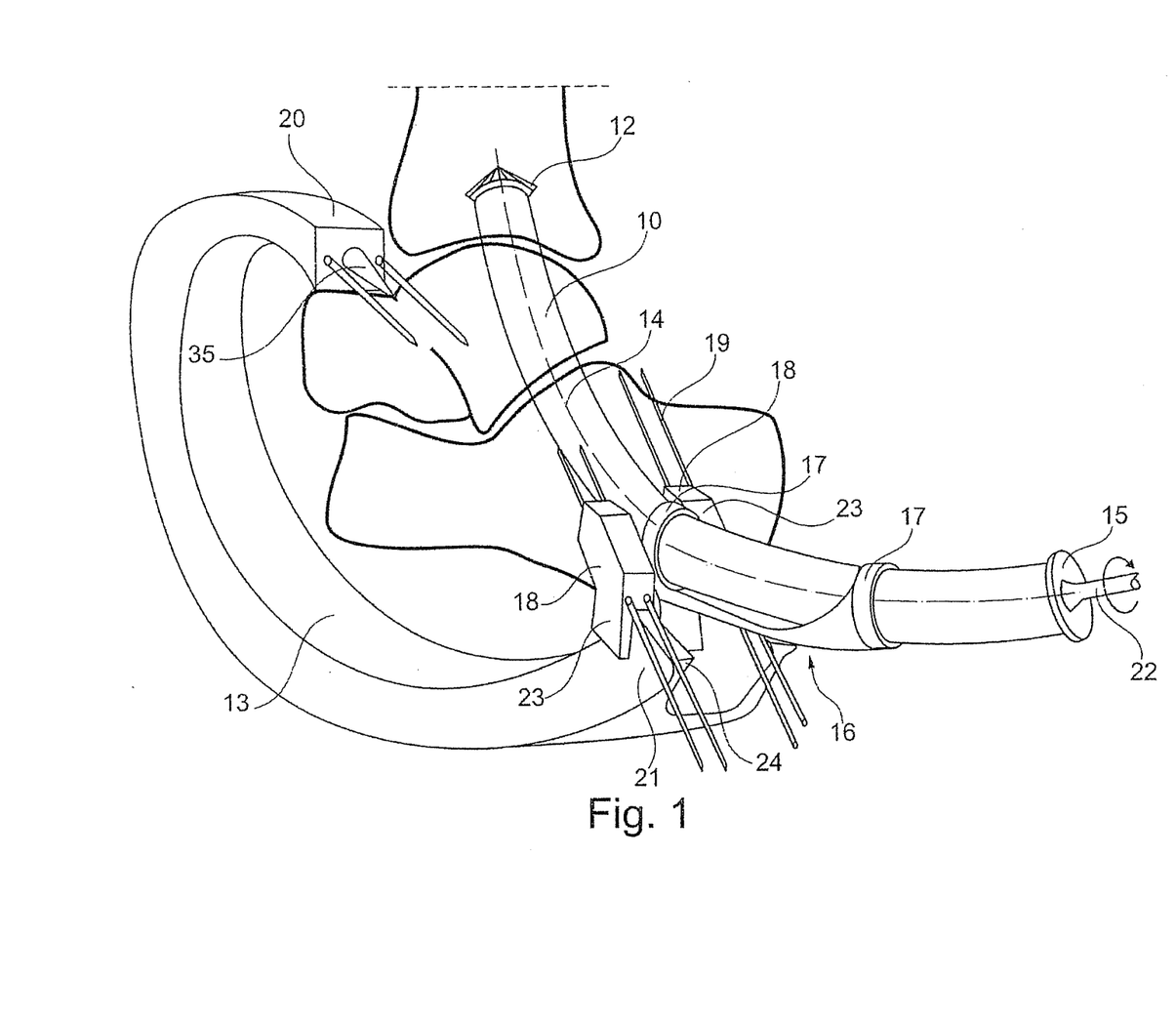
FIG. 1 shows a perspective view of a device according to an embodiment of the invention.
Figure 2:
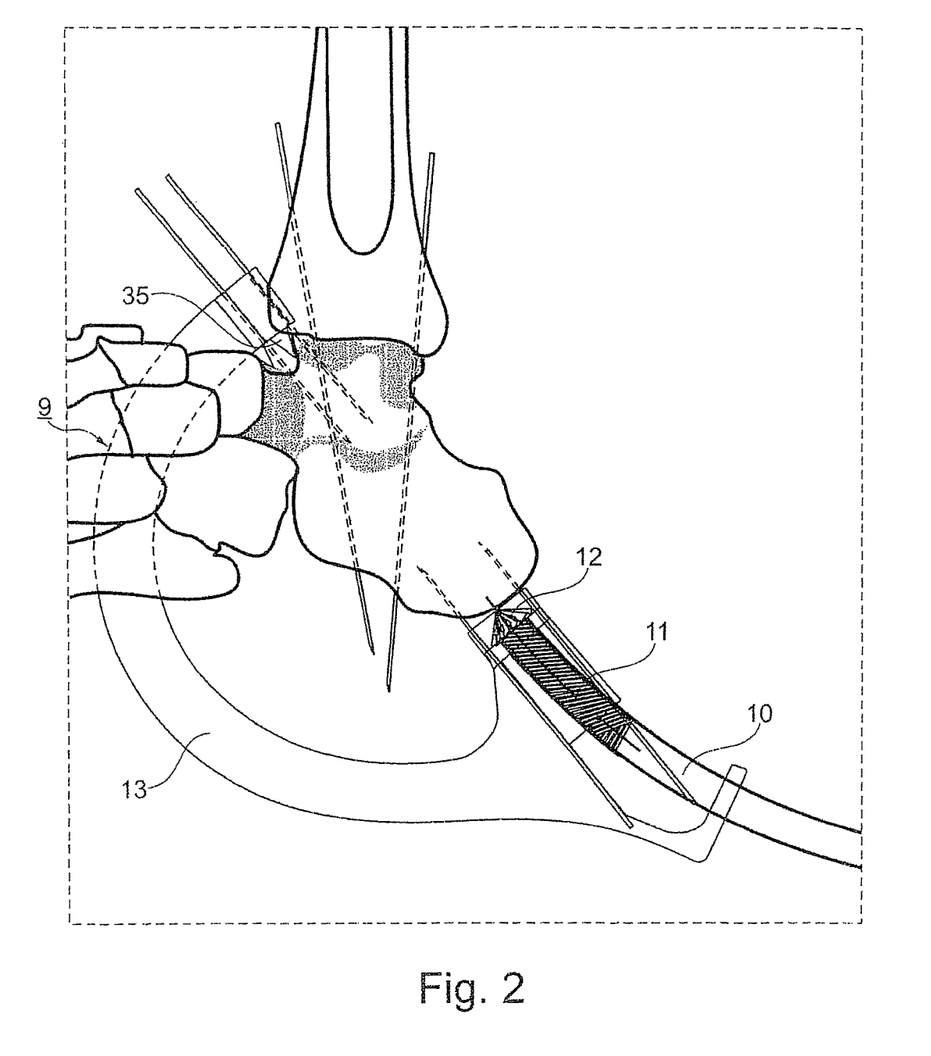
FIG. 2 shows a schematic side view of the device according to the embodiment of the invention shown in FIG. 1.
Figure 3:
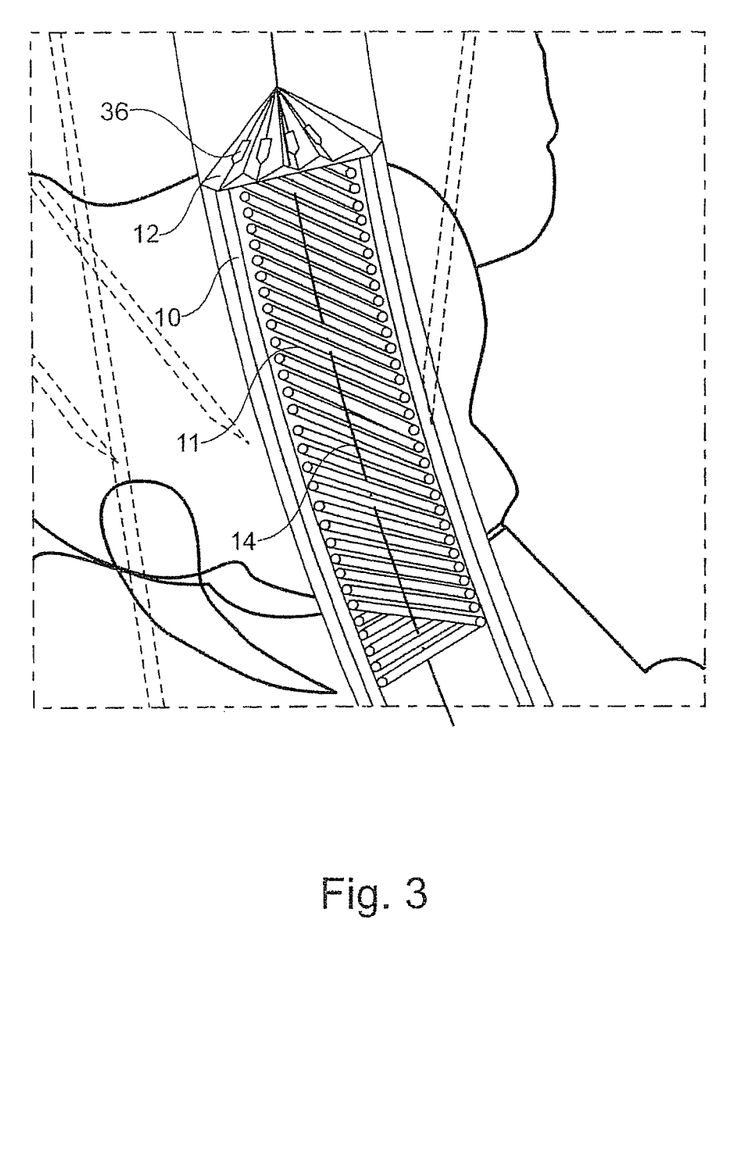
FIG. 3 shows a partial view including a tool head of the device according to the embodiment of the invention shown in FIG. 1.
Figure 4:
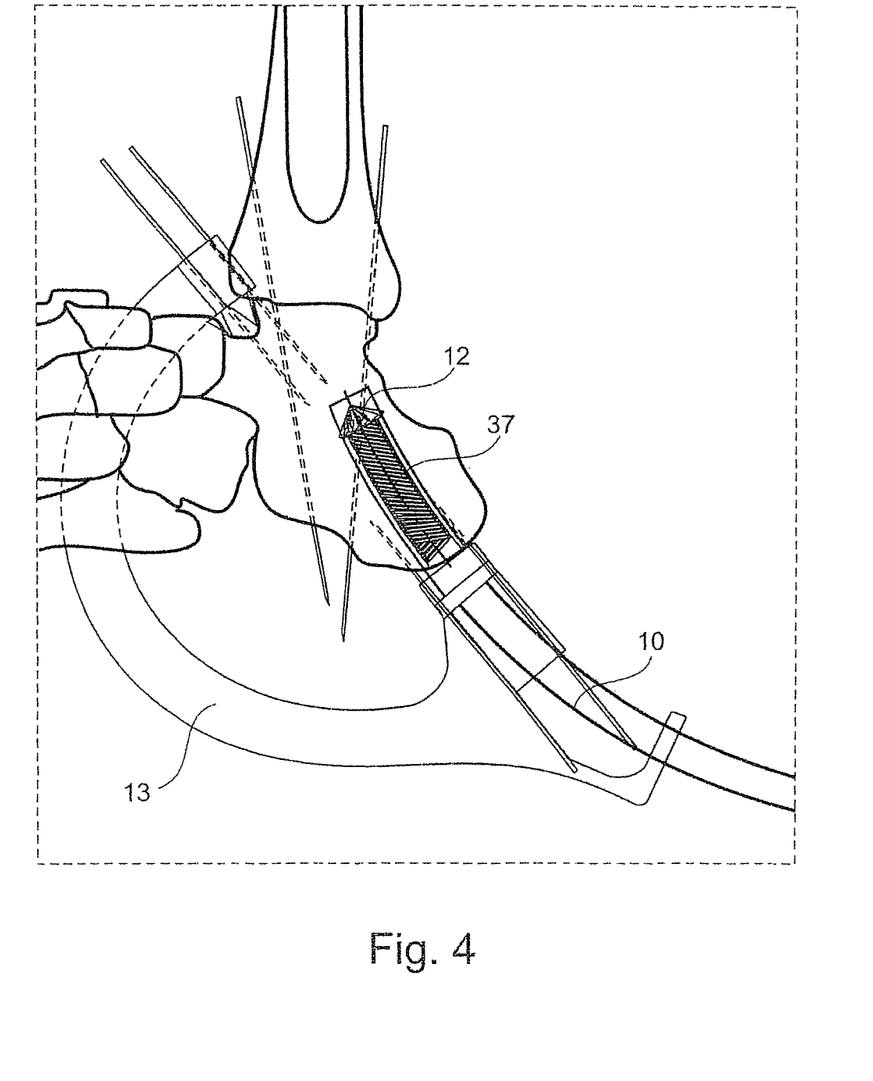
FIG. 4 shows a schematic side view of the device according to the embodiment of the invention shown in FIG. 1, with a partially completed bore in the bone.
Figure 5:
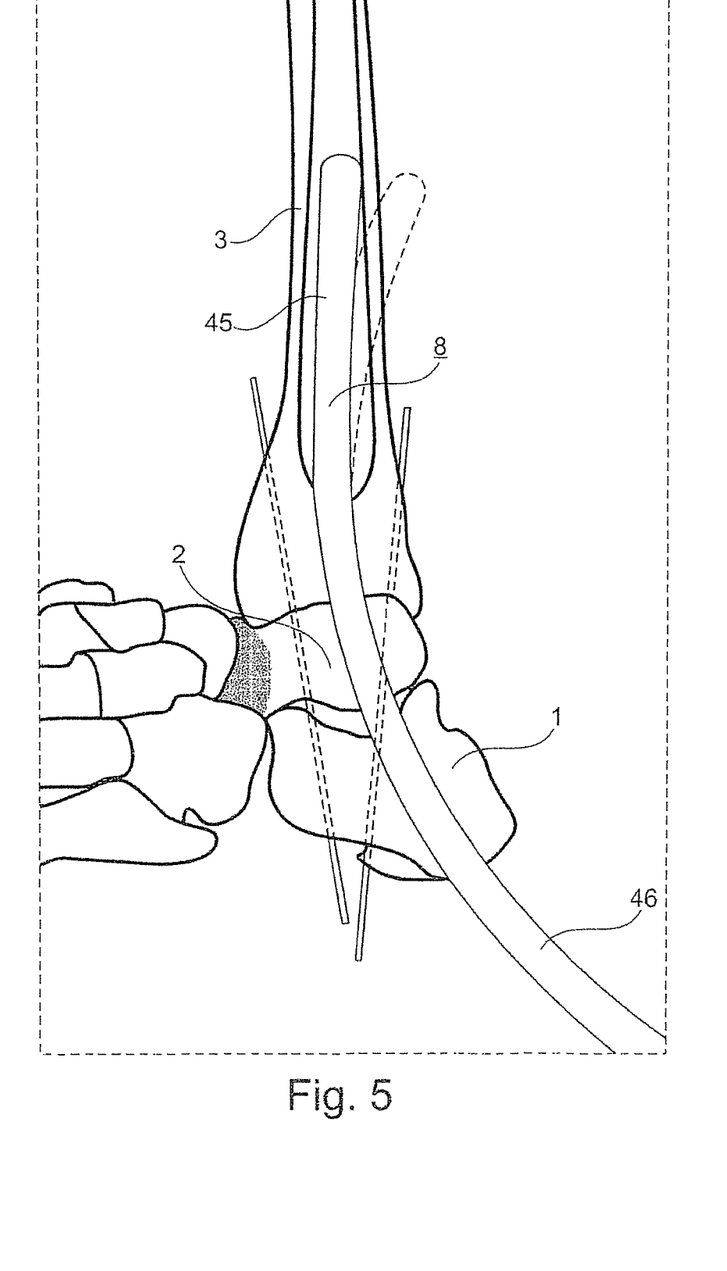
FIG. 5 shows a bone nail according to an embodiment of the invention, which has partially been inserted into the bone.

FIG. 5 shows the lower leg (crus) in a position, in which it may be rotated by about 45° in an inward direction. Those bones which are relevant for the application of an implant 8 according to embodiments of the invention have been illustrated. Substantially pictured are the calcaneus 1, the talus 2 and the tibia 3. In FIG. 5, a bone nail formed as an implant 8 according to an embodiment of the invention, is inserted through the calcaneus 1 and the talus 2, and may be partially inserted up until a lower part of the tibia 3. Prior to implantation, a front part 45 of the implant 8 has a curved shape (illustrated by a dashed line) having the same radius R of curvature as a rear part 46. Due to the reduced stiffness of the front part 45, this part may bend or deform during insertion into the tibia 3, such that the front part 45 can have a substantially larger radius of curvature after implantation, or may even have a rectilinear form.

Figure 6:
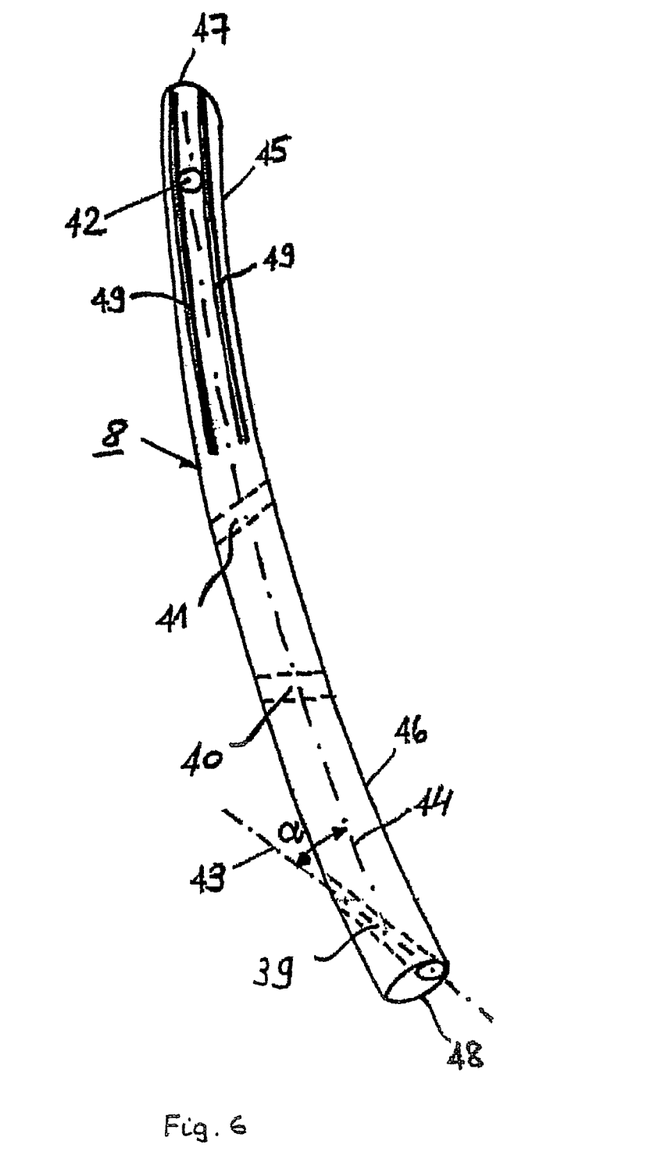
FIG. 6 shows a schematic view of the bone nail of FIG. 2 according to an embodiment of the invention.
Figures 7, 8, 9, 10:
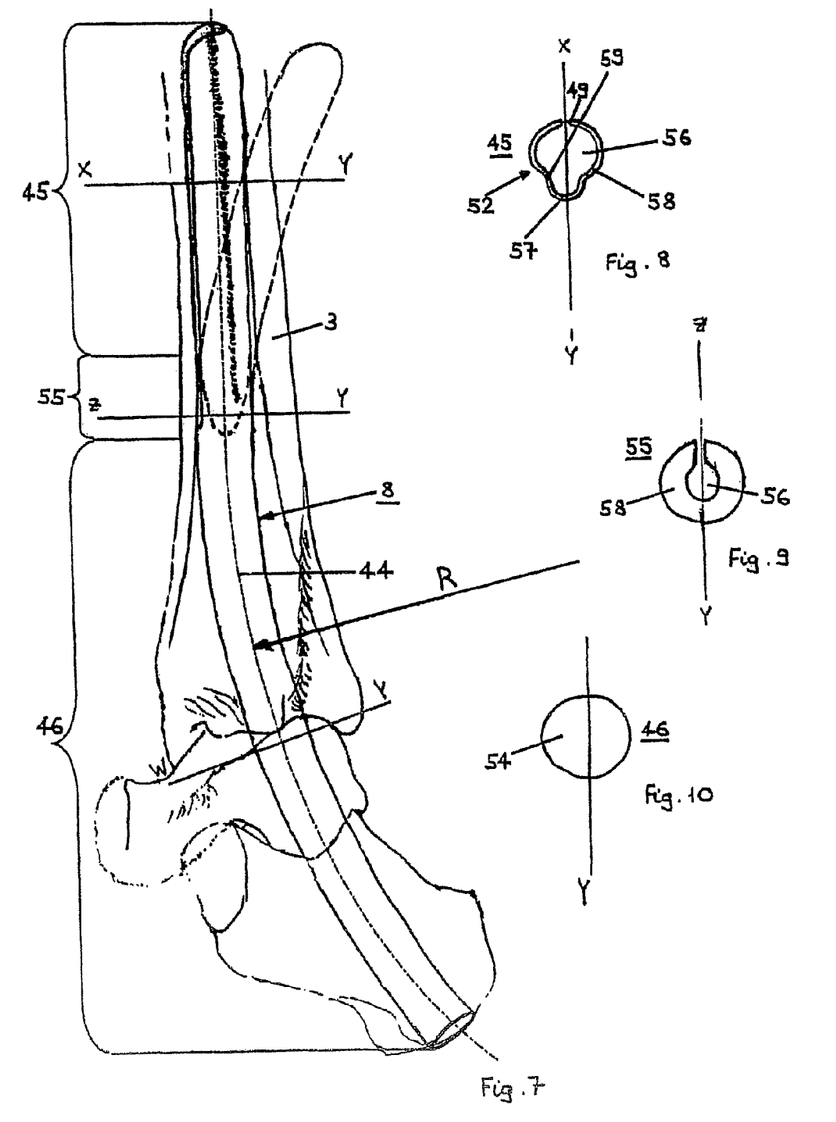
FIG. 7 shows a schematic view from an antero-lateral perspective of a bone nail implanted into the bone according to another embodiment of the invention.
FIG. 8 shows a cross-section at line X-Y of FIG. 7.
FIG. 9 shows a cross-section at the line Z-Y of FIG. 7.
FIG. 10 shows a cross-section at the line W-Y of FIG. 7.

As shown in FIG. 6, the implant 8 may be steadily curved within a plane having a radius R of curvature of typically 190 nun. The curvature extends over the entire length $L_I$ of the implant 8, which may typically be 140 mm. Its diameter $D_I$ may typically be 11 mm. The ratio $L_I/D_I$ between length $L_I$ and diameter $D_I$ of the implant 8 may typically be 12.7. The implant 8 comprises a number of transverse bores 39, 40, 41, 42, into which locking screws 30, 31, 32 can be inserted, as illustrated in, for example, FIG. 11k. Three of the transverse bores 39, 40, 41 may be positioned in a same plane as a plane in which the implant 8 is curved. A fourth transverse bore 42 may be positioned at a proximal end of the implant 8 and extend orthogonally to the said plane of curvature. In one embodiment, a longitudinal axis 43 of the transverse bore 39 which is positioned at the distal end of the implant 8 may be at an angle α of 15° with respect to a longitudinal axis 44 of the implant 8.

The implant 8 may be made of a particularly flexurally rigid material. At the front part 45 of the implant 8, longitudinal slits 49 are provided, such that the front part 45 of the implant 8 is formed as being more elastically bendable.

In order to insert the implant 8 into the bone, it may be advantageous, depending on the quality of the bones, to first drill the respective bones 1, 2, 3, by using the device 9 illustrated in FIGS. 1 through 4.

In FIGS. 7-10 there is illustrated a further embodiment of the implant 8, embodied as a bone nail, which differs from the embodiment according to FIG. 6 in that the bone nail in FIGS. 7-10:

a) has a shamrock-shaped cross-section 52 (see, e.g., FIG. 8) in a front part 45, a cavity 56 parallel to the longitudinal axis 44, and a longitudinal slit 49 parallel to the longitudinal axis 44; and b) has an intermediate part 55 between the front part 45 and a rear part 46, the intermediate part 55 formed as a transitional section between the front part 45 having a lower stiffness and the rear part 46 having a greater stiffness, such that the stiffness of the bone nail increases continuously towards the rear part 46.

Due to the cavity 56 the bone nail has a thin-walled cross-section 52 in the front part 45 including a peripheral wall 58 having a reduced wall thickness, which is further separated by the longitudinal slit 49 parallel to the longitudinal axis 44. The shamrock-shape in the cross-section 52 results from the embodiment of the wall 58 having two indentations 59 extending parallel to the longitudinal axis 44. The two indentations 59 are arranged on the circumference such that a convex bend 57 of the wall 58 is formed, which diametrally opposes the longitudinal slit 49 and extends parallel to the longitudinal axis. In the intermediate part 55 the stiffness increases from the front part 45 towards the rear part 46 due to a wall thickness of the wall 58 increasing towards the rear part 46. This growing wall thickness is achieved by a continuous narrowing of the cavity 56, and by continuously decreasing the radially measured depth of the indentations 59 in the wall 58 towards the rear part 46, such that there is a continuous transition from the shamrock-shaped cross-section 52 of the front part 45 towards the circular-shaped cross-section 54 of the rear part 46. Prior to the implantation the intermediate part 55 and the front part 45 of the bone nail may have a curved shape (illustrated by a dashed line) having a same radius R of curvature as the rear part 46. Due to the reduced stiffness of the intermediate part 55 and in particular of the front part 45, these sections may bend or deform during insertion into the tibia 3, such that the front part 45 may be bent to have a substantially larger radius of curvature after implantation, or may even may have a rectilinear form (see, e.g., FIG. 7).

The following is a description of a surgery technique according to an embodiment of the invention, with reference to FIGS. 11a to 11k.

Figure 11A:
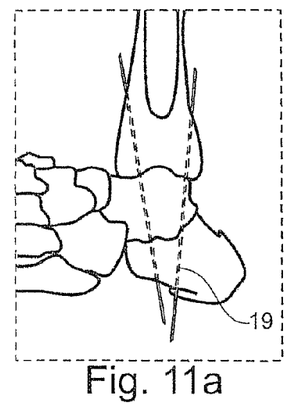
FIGS. 11a-11k show schematic drawings of a method of using the device according to an embodiment of the invention.

A patient is brought to a dorsal, ventral or lateral position. By virtue of a selective, limited, front-, lateral- or postero-lateral aditus, both joints (upper and subtalar) are tackled, whereby remaining cartilage is removed. Tibia 3, talus 2 and calcaneus 1 should be freely movable at this point, to achieve a desired re-orientation (alignment). The destroyed and/or to be treated joints or other target joints are aligned (by means of, for example, Arthrodesis between the calcaneus, talus and tibia). A selected position may be fixed by percutaneously inserted, rigid Kirschner wires 19 (3 mm diameter in one embodiment), as shown in FIG. 11a. An aditus of about 2-3 cm length is formed at the lateral heel. A margin of the postero-lateral Calcaneus (tuber calcanei) is located.

Figure 11B:
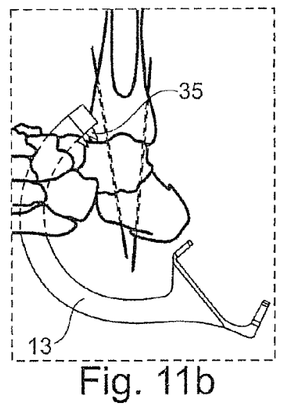
Figure 11C:
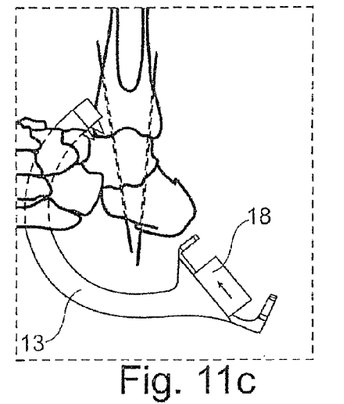
Figure 11D:
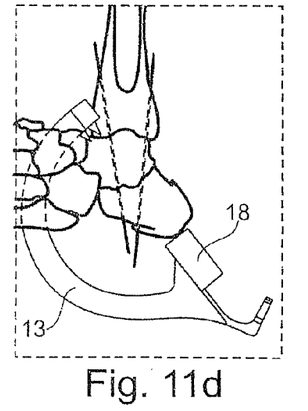
Figure 11E:
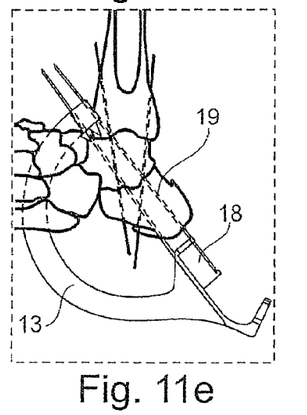

The target device 13 may be attached, with the tip 35 of the target device 13 at the medial base of the upper subtalar joint, as shown in FIG. 11b. The fixation carriage 18 is assembled to the target device 13 as shown in FIG. 11c. The fixation carriage 18 is moved (e.g., via sliding) near the skin at the aditus, as shown in FIG. 11d. The target device 13, with the fixation carriage 18, can further be fixed at the heel using the Kirschner wires 19, as shown in FIG. 11e.

Figure 11F:
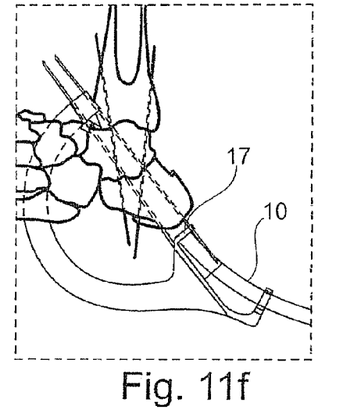
Figure 11G:
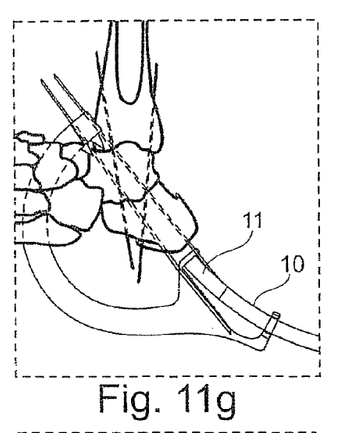
Figure 11H:
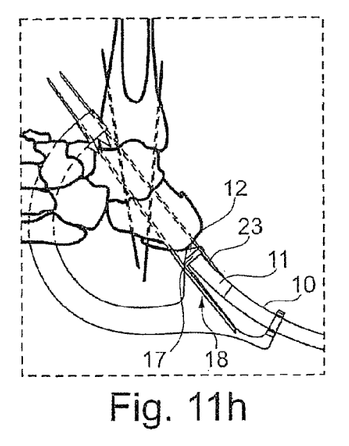
Figure 11I:
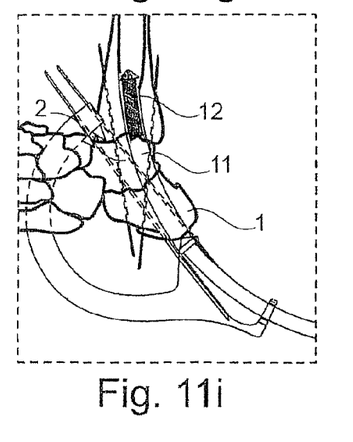

The stiff tube 10 may be inserted into the two target rings 17, as shown in FIG. 11f. The flexible shaft 11 may be inserted into the stiff tube 10, as shown in FIG. 11g. The tool head 12 is mounted at the front end of the flexible shaft 11 and inserted into a bone opening, as shown in FIG. 11h. The tool head 12 may be inserted between the foot surface and the front target ring 17 and between the two jaws 23 of the fixation carriage 18, and may be mounted at the flexible shaft 11 under pre-tension of the flexible shaft 11. For this purpose the tube 10 and the flexible shaft 11 are fed into the two target rings 17 until the front end of the tube 10 and the flexible shaft 11 align with an end face of the front target ring 17. The bore for the implant 8 is milled by the simultaneous rotation and feeding or pushing of the flexible shaft 11, traversing the calcaneus 1 and the talus 2 at the level of the posterior subtala joint facet, until the tool head 12 enters into the tibia marrow space, as shown in FIG. 11i. The device 9 is disassembled.

Figure 11J:
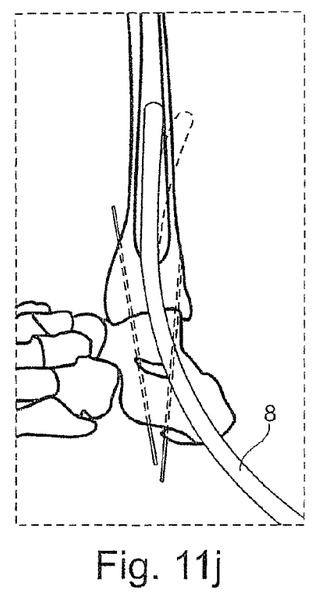
Figure 11K:
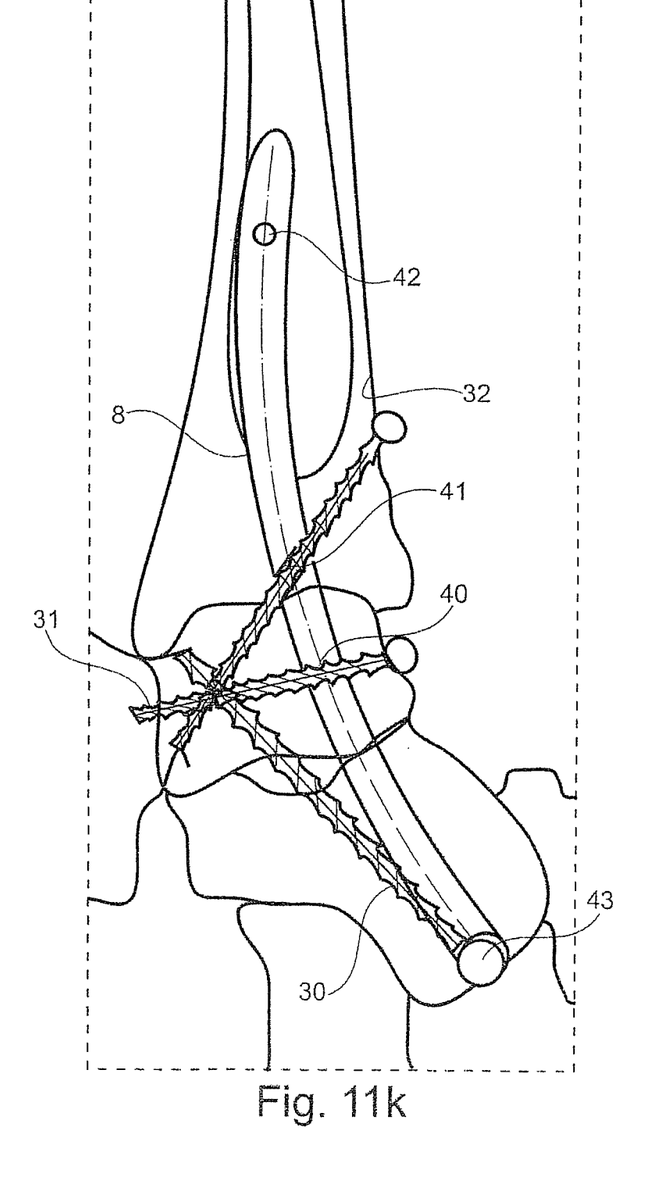

An implant 8 may be inserted into the bore up until it reaches the Tibia marrow cavity, as shown in FIG. 11j. This can be accomplished by means of inserting the implant 8 with an optional target handle (not illustrated), which may include guides for drilling bores for locking screws 30, 31, 32. A nail 33 may be driven or advanced until its front part 45 plastically extends into the tibia marrow cavity, as shown in FIG. 5. The optional locking screws 30, 31, 32 for the calcaneus 1, the talus 2 and the tibia 3 may be percutaneously inserted, as shown in FIG. 11k. The skin can be sutured, and the procedure is completed.

In FIG. 11k the foot is rotated inwards with the lower leg by about 45°. The implant 8 is illustrated in its finally implanted position. The first locking screw 30 in the transverse bore 39 secures the implant 8 in the calcaneus 1 and in the talus 2. The second locking screw 31 in the transverse bore 40 blocks the implant 8 in the Talus 2. The third locking screw 32 in the transverse bore 41 blocks the implant 8 in the Tibia 3 and in the talus 2. Consequently, the three bones tibia 3, talus 2 and calcaneus 1 are held together stiffly, and more importantly, in an anatomically correct orientation.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A device for forming a circular arc-shaped bore in a bone of a foot of a body, comprising:
   a drilling device comprising:
      an arc-shaped member having a longitudinal axis, a radius of curvature of the longitudinal axis being within a range from 130 mm to 240 mm;
      a flexible shaft received in said member, said flexible shaft being more flexible than said member; and
      a head at a first end of the shaft; and a target device mountable to the foot, wherein the target device comprises:
a main body comprising a first section and a second section, wherein the first section comprises a first end that is mountable to the foot using a first mounting member and wherein the second section comprises a second end that is mountable to the foot using a second mounting member for clamping at least a portion of said foot between the first end of the first section and the second end and allowing the drilling device to drill an arc-shaped bore in said bone initiated from proximate the second end and extending in a direction toward the first end of the first section, wherein the first mounting member extends longitudinally along its longitudinal axis from the first end of the first section toward the second end, and wherein the second mounting member extends longitudinally along its longitudinal axis toward the first end of the first section.

2. The device according to claim 1, wherein a curvature of the arc-shaped member corresponds to the radius of curvature of the longitudinal axis.

3. The device according to claim 2, wherein the curvature of the arc-shaped member corresponds to each infinitesimal arc of the arc-shaped member.

4. The device according to claim 1, wherein the head has an outer diameter D, the arc-shaped member has an outer diameter $d_a$, and a ratio $d_a/D$ has a maximum value of 0.95.

5. The device according to claim 4, wherein the ratio $d_a/D$ does not exceed 0.92.

6. The device according to claim 1, wherein the first mounting member is a tip and the second mounting member comprises at least a wire extending therefrom.

7. The device according to claim 1, further comprising a circular arc-shaped guide for receiving the arc-shaped member and wherein the guide comprises two or more target rings.

8. The device according to claim 7, wherein the arc-shaped member is movable along the guide of the target device.

9. The device according to claim 1, wherein the head has at least one axial perforation for removing chips of bone material from the bore.

10. The device according to claim 1, further comprising a fixation device coupled to the second end, wherein the second mounting member extends longitudinally from the fixation device toward the first end.

11. The device according to claim 10, wherein the fixation device is slideable relative to second section.

12. The device according to claim 11, wherein the fixation device comprises first and second jaws and wherein the main body comprises a first guide and a second guide at the second section, wherein the first jaw is slideable along the first guide and the second jaw is slideable along the second guide.

13. The device according to claim 12, further comprising a third guide for receiving the tube said third guide being sandwiched between said first and second jaws.

14. The device according to claim 1, wherein the head is mountable to said first end of the shaft.

15. The device according to claim 1, wherein the arc-shaped member is a unitary structure.

16. The device according to claim 1, wherein the first mounting member comprises a first piece and a second piece.

17. The device according to claim 16, wherein the first piece is a tip and the second piece is a wire.

18. The device according to claim 16, wherein the second mounting member comprises a first piece and a second piece.

19. The device according to claim 18, wherein the first piece is carriage and the second piece is a wire.

20. A kit comprising:
a device for forming a circular arc-shaped bore in a bone of a foot, comprising:
a drilling device comprising
an arc-shaped member having a longitudinal axis, a radius of curvature of the longitudinal axis being within a range from 130 mm to 240 mm;
a flexible shaft received in said member, said flexible shaft being more flexible than said member; and
a head at a first end of the shaft; and
a target device mountable to the foot, wherein the target device comprises
a main body comprising a first section and a second section, wherein the first section comprises a first end having a first mounting member extending longitudinally therefrom that is mountable to the foot and wherein the second section comprises a second end and a second mounting member extending longitudinally therefrom that is mountable to the foot for clamping at least a portion of said foot between the first end of the first section and the second end and allowing the drilling device to drill an arc-shaped bore in said bone initiated from proximate the second end and extending in a direction toward the first end of the first section, wherein the first mounting member extends longitudinally along its longitudinal axis from the first end of the first section toward the second end and the second mounting member extends longitudinally along its longitudinal axis toward the first end of the first section; and
at least one implant configured to be curved in a plane comprising:
a front part for insertion into a bone and comprising a tip; and
a rear part comprising an end.

21. The kit according to claim 20, wherein the at least one implant comprises a bone nail.

22. The kit according to claim 21, wherein the bone nail is configured to be implanted into a heel of a foot of a patient.

23. The kit according to claim 20, wherein the implant is stiff from the end of the rear part to at least 120 mm from the end of the rear part.

24. The kit according to claim 20, wherein the implant has a radius of curvature of at least 130 mm.

25. The kit according to claim 24, wherein the curvature of the implant corresponds to each infinitesimal arc of the implant.

26. The kit according to claim 20, further comprising a fixation device coupled to the second end, wherein the second mounting member extends longitudinally from the fixation device toward the first end.

27. The kit according to claim 26, wherein the fixation device is slideable relative to second section.

28. The kit according to claim 20, wherein the head is mountable to said first end of the shaft.

29. The kit according to claim 20, wherein the arc-shaped member is a unitary structure.

30. A method of forming a circular-shaped bore in a first bone of a foot using a drilling device having an arc-shaped member having a longitudinal axis, a radius of curvature of the longitudinal axis being within a range from 130 mm to 240 mm, a flexible shaft and a head on the flexible shaft and a target device wherein the target device is coupled to the drilling device and comprises a main body comprising a first section comprising a first end and a first mounting member extending longitudinally therefrom, and a second section comprising a second end and a second mounting member extending longitudinally therefrom, wherein at least a portion of the flexible shaft is within the arc-shaped member, the method comprising:

mounting the first section to the first bone of the foot with the first mounting member;

mounting the second section to a second bone of the foot with the second mounting member so that the first mounting member extends longitudinally along its longitudinal axis from the first end toward the second end and the second mounting member extends longitudinally along its longitudinal axis toward the first end clamping at least a portion of the foot between the first end the and the second end;

and pushing the head into the first bone of the foot proximate the first section toward the second end.

31. The method according to claim 30, wherein the forming of the circular-shaped bore is for facilitating tibiocalcaneal arthrodesis.

32. The method according to claim 30, wherein the first bone is a calcaneus and the second bone is a talus.

33. The method according to claim 30, further comprising mounting the head on the flexible shaft.

34. A method of forming a circular-shaped bore in a bone of a foot using a drilling device having a stiff circular arc-shaped tube having a central axis, the radius of curvature of the central axis being within a range from 130 mm to 240 mm, a flexible shaft and a head and a target device wherein the target device is coupled to the drilling device and comprises a main body comprising a first section comprising a first end and a second section comprising a second end and a fixation device, wherein said main body has a generally channel shape between the first and second ends, the method comprising:

mounting the first end to the bone of the foot;

mounting the fixation device to the foot by moving said fixation device relative to the second section, clamping at least a portion of the foot between the first end and the fixation device;

inserting the flexible shaft into the arc-shaped tube;

mounting the head to a first end of the shaft; and pushing the head into the first bone of the foot proximate the fixation device toward the first end.

35. The method according to claim 34, wherein moving said fixation device relative to the second section comprises sliding said fixation device along the second end.

\* \* \* \* \*

UNITED STATES PATENT AND TRADEMARK OFFICE
CERTIFICATE OF CORRECTION

PATENT NO.        : 9,522,009 B2  
APPLICATION NO.   : 12/781168  
DATED             : December 20, 2016  
INVENTOR(S)       : Kaj Klaue Page 1 of 1

It is certified that error appears in the above-identified patent and that said Letters Patent is hereby corrected as shown below:

In the Specification

Column 2, Line 60    Delete "[tube: $I=I_y=\pi\ (d_a^4-d_1^4/64]$"  
Insert --[tube: $I = I_x = I_y = \pi\ (d_a^4-d_i^4)/64$]--

Column 3, Line 65    Delete "$I_x = 12\ mm^4$"  
Insert --$I_x = 121\ mm^4$--

Signed and Sealed this  
Twenty-second Day of May, 2018

Andrei Iancu  
*Director of the United States Patent and Trademark Office*